(12) United States Patent
Chin

(10) Patent No.: US 7,078,411 B2
(45) Date of Patent: Jul. 18, 2006

(54) PHOSPHOLIPID TRANSFER PROTEIN (PLTP) AND CHOLESTORAL METABOLISM

(75) Inventor: Khew-Voon Chin, Highland Park, NJ (US)

(73) Assignee: UMDNJ (Univ of Medicine & Dentist. of NJ), New Brunswick, NJ (US)

( * ) Notice: Subject to any disclaimer, the term of this patent is extended or adjusted under 35 U.S.C. 154(b) by 508 days.

(21) Appl. No.: 10/146,681

(22) Filed: May 15, 2002

(65) Prior Publication Data

US 2002/0187997 A1    Dec. 12, 2002

Related U.S. Application Data

(60) Provisional application No. 60/291,383, filed on May 16, 2001.

(51) Int. Cl.
*A61K 31/435*    (2006.01)

(52) U.S. Cl. ...................... 514/283; 514/824

(58) Field of Classification Search .................. 514/283
See application file for complete search history.

(56) References Cited

U.S. PATENT DOCUMENTS 5,622,843 A    4/1997    Day et al.

6,255,317 B1 *    7/2001    Kim et al. .................. 514/280

OTHER PUBLICATIONS

Bruce et al., 1998, Ann. Rev. Nutrition 18:297-330.
Nishida, H.I. et al., 1997, J. Biol. Chem. 272:6959-6964.
Wolfbauer, G. et al., 1999, Biochem. Biophys, Acta 1439: 65-76.
Tu, A. Y. et al, 1995, Biochem. Biophys. Res. Commun. 1207:552-558.
Whitmore, T.E. et al., 1995, Genomics 28:599-600.
Day, J.R. et al., 1994, J. Biol. Chem. 269:9388-9391.
Jiang, X.C. et al., 1999, J. Clin. Invest. 103:907-914.
Huuskonen, J. et al., 1999, J. Lipid. Invest. 40:1123-1130.
Tu, A. Y. et al., 1999, Int. J. Clin. Lab. Res. 29:14-21.
Jiang, X.C. et al., 1995, J. Biol. Chem, 270:17133-17138.

* cited by examiner

*Primary Examiner*—Barbara P. Badio
(74) *Attorney, Agent, or Firm*—Klauber & Jackson

(57) ABSTRACT

A method for controlling cholesterol metabolism in a host, a screening assay for agents that can control cholesterol metabolism, and the agents that may be identified are practiced and determined in relation to the expression of PLTP in HepG2 cells and a clone from these cells, designated HepG2/PLTPpLuc. Particular agents that are covered comprise camptothecin, topotecan, derivatives thereof, metabolic byproducts thereof and small molecule mimics thereof.

15 Claims, 16 Drawing Sheets

FIG. 6C (Sheet 1)

```
          10         20         30         40         50         60
  GATCACTTGA GGGCAGGAGT TCAAGACCAG CCTGGCCAAA ATGGCAAAAC CCTGTCTCCA 70         80         90        100        110        120
  CTAAAAATAC AAAAATTAGC CAGGTGTGGT GGCACATGGC TGTAGTCCCA GCTACTTGGG 130        140        150        160        170        180
  AGGCTGAGGC AGGAGAATCA CTTGAACCCA GGAGGCAGAG GTTGCAGTGA GCCAAGATCA 190        200        210        220        230        240
  CACCACCGCA CTGCAGCCTG GTGACAGAGC ACGACTGTGT CTCAAAAAAA TTAATTAATT 250        260        270        280        290        300
  AATTAAATAA AAAAGGAAAT GGAACTATTT TTGTGAATCT GTGGATTATA TCAGAAAAAA 310        320        330        340        350        360
  AAGACACAAT GGGGAAAGTC CTAGGCAAAT CAGGATGAGT TAGTCATCCT TCCTAGATGA 370        380        390        400        410        420
  GTGTTTGGTG CTAAATACAT GCTCAGCAGA CATGATTATT GCTTCCCCTT TCTTTCGTCC 430        440        450        460        470        480
  ATTTGGCAAC AAAAAGGTGG CAAGCACCCA CTCTGTGCCC TGTCCTAGGG TCCGGGAACC 490        500        510        520        530        540
  CTGTAAGCAG TAGATGGAGG TGGGGGTGGG GGTGGGGGCG GGGATGCTGT TCAGAGCACC 550        560        570        580        590        600
  TTGCTCCAAG GGTTCATTAA AAAATCCACC AGTGGACCGG GCGCGGTGGC TCATGCCTTT 610        620        630        640        650        660
  AATCCCAGCA CTTTGGGAGG CCGAGGCGGG CGGATCACAA GGTCAGGAGA TCGAGACCAT 670        680        690        700        710        720
  CCTGGCTAAC ACGGTGAAAC CCCGTCTCTA CTAAAAATAC AAAAAAAATT AGCGGGGCGT 730        740        750        760        770        780
  GGCAGCGTGC GCCTGTAGCC CCAGCTGCTG GGGAGGCTGA GGCAGGAGAA TGGCGTGAAC 790        800        810        820        830        840
  CCGGGAGGCG GGGCTTGCAG GGAGCCGAGA TCGCGCCACT GCACTCCAGC CTGGGGGACA 850        860        870        880        890        900
  GAGCGAGACT CCGTCTCAAA AAATAAAAAT AAAAAAAATA GAAAAAACAA TCCACCAGCC 910        920        930        940        950        960
  ACGATAAATG GCAGACCTCC TTCTGATTTC AGCCGGTGTG GTATGTTCCT GGGCTGACAG 970        980        990       1000       1010       1020
  CACTTGTCTA GTCTTGCTTT CCCAAGTGGG AAAGGTCTCT GGGACCTTAA GGTCCCCAGG 1030       1040       1050       1060       1070       1080
  TGGTGACACA GAGACAGGTA GGGGGGCCCA TAGCAAAGCC AGGCAAGGAG GTCCCGAGAT
```

FIG. 6C (Sheet 2)

```
          1090       1100       1110       1120       1130       1140
     GATTGTGGGT GGCAGGGAAA GAAAAAATAT TCCTTGACTT TGTGCCTGGA CCTGGTTGTA 1150       1160       1170       1180       1190       1200
     ATAAAGGCCC AAGAGGTAGT TCCTATCATC GTGCACATTT CGCTGAAGGA AGAAACTGAG 1210       1220       1230       1240       1250       1260
     GGTCAGTGAC CCAAGTGAAG TGACTTGCCC AAGATCATGC AGGAAGACAT GGATAATTGT 1270       1280       1290       1300       1310       1320
     AATTTGAACC AAGGTCCCAG CAAAGTGGGA TTGTTGGGGC TGAGTGGGCC GGCTCCTGCA 1330       1340       1350       1360       1370       1380
     TTTCCTTCCC TCTCCCTGGG CTTGGGTCTC CCACTTGTCC AGACAGCGGC CGGGCTTGTC 1390       1400       1410       1420       1430       1440
     ACGGGGCTCT GTGCAGCCTT TTCCACTCTC CCGGCTGCCA GCGTCCCGCC CCGTCCCCTC 1450       1460       1470       1480       1490       1500
     CCAGCCCCCA AGGGAGGAGG GGAGAGCTGC AGAGAGGAGG AGGGGTCGGG GAGGCCGGCT 1510       1520       1530       1540       1550       1553
     TTATAAAGGC GGCTGGAACA ACCCTGCCCG CCAGACCCCG TCGCCCGGAT CCC
```

**Function of PLTP
Reverse Cholesterol Transport**

Triglyceride Rich lipoproteins

Secretion into Bile Acid

SEQUENCE LISTING

<160> NUMBER OF SEQ ID NOS: 1

<210> SEQ ID NO 1
<211> LENGTH: 1553
<212> TYPE: DNA
<213> ORGANISM: homo sapiens

<400> SEQUENCE: 1

```
gatcacttga gggcaggagt tcaagaccag cctggccaaa atggcaaaac cctgtctcca      60
ctaaaaatac aaaaattagc caggtgtggt ggcacatggc tgtagtccca gctacttggg     120
aggctgaggc aggagaatca cttgaaccca ggaggcagag gttgcagtga gccaagatca     180
caccaccgca ctgcagcctg gtgacagagc acgactgtgt ctcaaaaaaa ttaattaatt     240
aattaaataa aaaaggaaat ggaactattt ttgtgaatct gtggattata tcagaaaaaa     300
aagacacaat ggggaaagtc ctaggcaaat caggatgagt tagtcatcct tcctagatga     360
gtgtttggtg ctaaatacat gctcagcaga catgattatt gcttcccctt tctttcgtcc     420
atttggcaac aaaaaggtgg caagcaccca ctctgtgccc tgtcctaggg tccgggaacc     480
ctgtaagcag tagatggagg tgggggtggg ggtggggcg gggatgctgt tcagagcacc     540
ttgctccaag ggttcattaa aaaatccacc agtggaccgg gcgcggtggc tcatgccttt     600
aatcccagca ctttgggagg ccgaggcggg cggatcacaa ggtcaggaga tcgagaccat     660
cctggctaac acgtgaaac cccgtctcta ctaaaaatac aaaaaaatt agccgggcgt      720 ggcagcgtgc gcctgtagcc ccagctgctg gggaggctga ggcaggagaa tggcgtgaac     780
ccgggaggcg gggcttgcag ggagccgaga tcgcgccact gcactccagc ctgggggaca     840
gagcgagact ccgtctcaaa aaataaaaat aaaaaaaata gaaaaaacaa tccaccagcc     900
acgataaatg gcagacctcc ttctgatttc agccggtgtg gtatgttcct gggctgacag     960
cacttgtcta gtcttgcttt cccaagtggg aaaggtctct gggaccttaa ggtccccagg    1020
tggtgacaca gagacaggta gggggccca tagcaaagcc aggcaaggag gtcccgagat    1080
gattgtgggt ggcagggaaa gaaaaaatat tccttgactt tgtgcctgga cctggttgta    1140
ataaaggccc aagaggtagt tcctatcatc gtgcacattt cgctgaagga agaaactgag    1200
ggtcagtgac ccaagtgaag tgacttgccc aagatcatgc aggaagacat ggataattgt    1260
aatttgaacc aaggtcccag caaagtggga ttgttgggc tgagtgggcc ggctcctgca    1320
tttccttccc tctccctggg cttgggtctc ccacttgtcc agacagcggc cgggcttgtc    1380
```

```
                                                                     -continued acggggctct gtgcagcctt ttccactctc ccggctgcca gcgtcccgcc ccgtcccctc    1440
ccagccccca agggaggagg ggagagctgc agagaggagg aggggtcggg gaggccggct    1500
ttataaaggc ggctggaaca accctgcccg ccagacaccg tcgcccggat ccc           1553
```

PHOSPHOLIPID TRANSFER PROTEIN (PLTP) AND CHOLESTORAL METABOLISM

CROSS-REFERENCE TO RELATED APPLICATION

This application claims benefit of priority to provisional application Ser. No. 60/291,383, filed May 16, 2001, which is incorporated herein by reference in its entirety.

FIELD OF THE INVENTION

The present invention relates generally to cholesterol metabolism, and more particularly, to the reduction of serum cholesterol, and particularly, the discovery of new drugs and agents that can achieve this objective. Moreover, new genetic constructs have been developed useful for screening for new drugs and agents that can be used to treat diseases associated with high levels of cholesterol.

DESCRIPTION OF THE RELATED ART

The presence of abnormally high serum cholesterol in humans is clearly associated with a variety of pathologies including coronary heart disease, atherosclerosis, hypercholesterolemia and particularly rare forms of these conditions that have defied effective treatment in the past, namely Tangier disease and familial high density lipoprotein (HDL) deficiency. The last mentioned conditions are both characterized by a low concentration of circulating HDL, which are generally thought of as effecting transport and transition of cholesterol for metabolic conversion in the liver to bile acids and, thereafter, for removal from the body.

The ability to modulate the level of cholesterol in the serum would have beneficial consequences in other conditions attributed to the presence of abnormally high cholesterol levels, such as atherosclerosis, stroke and the like. In this connection, U.S. Pat. No. 5,622,843 to Day et al identifies phospholipid transfer protein (PLTP) as a possible actor in lipid transfer and particularly, as a possible regulator of HDL as well as LDL metabolism. Day et al suggest that PLTP may be useful per se as a diagnostic and research tool, and that its examination in conjunction with HDL may elucidate the mechanisms of action that will hold the key for the development of new therapeutic approaches to this problem. While Day et al identified the sequence and structure of PLTP, they readily acknowledge that the need continues to exist for effective new treatment modalities that will achieve cholesterol metabolism homeostasis. It is to the achievement of this and other related objectives that the present invention is directed.

SUMMARY OF THE INVENTION

In accordance with the present invention the interaction of phospholipid transfer protein (PLTP) with certain pharmaceutical agents comprising camptothecin derivatives has been conducted initially, in connection with drug resistance studies, and it has been unexpectedly found that certain of the derivatives and particularly, the derivative identified as topotecan causes an increase in the expression of PLTP particularly, in human hepatocellular blastoma HepG2 cells, with the result that these increases in PLTP expression confer a corresponding increase in cholesterol transport for breakdown in the liver to bile acid and subsequent removal from the system. The specific interaction of this derivative and PLTP has prompted the identification of the first and primary aspect of the present invention, which is the screening and identification of other agents, including small molecules, that will serve as activators of PLTP expression and that will thereby confer beneficial adjustment to serum cholesterol levels in a host.

Accordingly, in a further aspect of the present invention a method for regulating and normalizing cholesterol metabolism in a host is disclosed which comprises promoting the increased expression of PLTP in the host. More particularly, the method comprises the administration of a cholesterol metabolism normalizing amount of an agent which promotes increased PLTP expression which agent is selected from the group consisting of camptothecin, topotecan, enantiomers thereof, derivatives thereof, metabolic byproducts thereof and small molecule mimics thereof. The method as stated contemplates that increased PLTP expression by itself, will assist in cholesterol transport and disposal. This is particularly relevant in the instance of the rare disease conditions that are characterized by abnormally low levels of HDL in the host system.

In a further aspect of the method, the increased circulating levels of PLTP may function in conjunction with HDL in the instance where the levels of the latter are normal in the patient, to assist in the transport of cholesterol by both proteins to the liver for disposal. Thus, the present method is applicable to the treatment of a broad range of conditions associated with abnormally high levels of serum cholesterol, including coronary heart disease and atherosclerosis, as well as for the treatment of individuals who have exhibited refractory response to presently extant cholesterol modulating agents.

The present invention is also effective to treat conditions where genetic defects such as lowered or non-existent HDL levels, or the reduced presence or the absence of LDL receptors (LDL receptor$^{+/-}$ or LDL receptor$^{-/-}$), are exhibited. Two conditions reflective of HDL deficiency are the specific conditions of familial hypercholesterolemia (FH) and Tangier's disease, and both may be treated by the method of the present invention.

In a further aspect of the present invention, camptothecin derivatives as defined above could be administered either alone or in combinations, or further, with known lipid lowering agents such as the statins, niacin, bile acid-binding resins, fibrate and the like, to treat hyperlipidemias and hyperlipoproteinemias. In this manner, traditional treatment modalities could be augmented by the enhancement of PLTP action. The methods would target the entire range of lipid metabolism derangements, including those mentioned earlier, that are uniquely attributable to genetically lowered levels of HDL.

In a still further aspect of the present invention, the invention covers the identification, discovery and synthesis of agents such as camptothecin derivatives, enantiomers thereof, metabolic byproducts thereof and small molecule mimics thereof that are effective to lower cholesterol levels in a host or patient. In this connection, the active sites of the camptothecin derivatives and their metabolic byproducts could be determined and appropriate small molecules may be capable of discovery on that basis. More particularly and in accordance with the further aspect of the present invention, a screening assay and corresponding method is disclosed and is useful herein, which involves the preparation of a particular promoter construct containing genomic DNA from PLTP, which is then transfected into HepG2 cells, after which the cells are exposed to possible expression enhancing agents and examination subsequently is made to determine whether expression levels of PLTP were found to increase significantly.

In a further aspect of the present invention the invention extends to camptothecin derivatives, topotecan, their derivatives, their enantiomers, their metabolic byproducts, small molecule mimics thereof and mixtures thereof, that function to enhance cholesterol metabolism by interacting with and promoting the increased expression of PLTP. In a particular aspect of the invention, the agents in question are believed to promote transcription of PLTP. Accordingly, and in a related aspect of the invention therefore, a further aspect of the invention may extend to the enhancement of PLTP expression by the insertion into PLTP expressing cells of a particular promoter that will function to achieve expression enhancement or increase. As described above and later on herein, the promoter may be constituted of a portion or the entirety of the DNA encoding PLTP. In the instance where the promoter is used for an assay, an appropriate reporter gene such as the luciferase gene, may be included in the construct.

Thus, another aspect of the present invention is the use of a reporter construct containing a phospholipid transfer protein gene promoter associated with a reporter gene and a resistance marker gene for selection and identification of clones containing the reporter construct.

In yet another aspect of the invention, cell lines, and clones of these cell lines, can be prepared containing such constructs, and these cell lines and clones of these cell lines can be used in high throughput screening assays for identification of agents and small molecules that increase levels of the phospholipid transfer protein pharmacologically.

In yet another aspect of the invention, a process can be developed for monitoring the pharmacological regulation of phospholipid transfer protein gene promoter activity by measuring the expression of a reporter gene, the reporter gene being expressed by the cell line containing the reporter construct.

The present invention utilizes a reporter construct comprising the phospholipid transfer protein gene promoter associated with a reporter gene and a resistance marker gene for selection and identification of clones containing the reporter construct. This aspect of the invention can be utilized to identify non-toxic derivatives, enantiomers, or metabolites of camptothecin that have a profound effect on lowering plasma cholesterol, by enhancing reverse cholesterol transport via HDL.

Moreover, agents and small molecules identified through use of the high throughput screening assay may be used as adjunct therapy with other agents that lower plasma cholesterol through a different mechanism.

The present invention offers new strategies for the treatment of abnormalities in cholesterol metabolism, including new drugs that are specific for that purpose and corresponding drug discovery tools. The interaction between the camptothecin derivatives and PLTP in conjunction with the human HepG2 cells has never been identified before and offers the promise an efficient and highly effective strategy for scientific and clinical advances with respect to cholesterol monitoring and maintenance.

Accordingly, it is a principle object of the present invention to provide a method for the control and normalization of cholesterol metabolism which is effective in controlling cholesterol transport and normalizing cholesterol levels.

It is a further object of the present invention to provide a method for treatment as aforesaid that is effective with individuals having genetic deficiency in HDL capacity and capability.

It is a further object of the present invention to provide a method for treating pathologies associated with elevated cholesterol levels, such as atherosclerosis, by the administration of an agent that promotes increased expression of PLTP.

It is yet a further object of the present invention to provide a method for estimating the course and extent of the diseases such as Tangier's disease, familial HDL deficiency disease, and other diseases associated with deficiencies in uptake and removal of lipid molecules in a mammal by measuring the presence and amount of phospholipid transfer protein in said mammal.

It is yet a further object of the present invention to provide agents, including small molecules that are capable of promoting and increasing PLTP expression.

It is a still further object of the present invention to provide an assay, including, but not limited to, a high throughput screening assay, for the identification and discovery of agents including small molecules that are capable of enhancing and increasing PLTP expression. Moreover, said agents identified by said assay may be used to treat Tangier's disease, familial HDL deficiency disease, and other diseases associated with deficiencies in uptake and removal of lipid molecules in a mammal.

It is a still further aspect of the invention to prepare a test kit to be used for the detection and/or determination of one of the components selected from the group consisting of phospholipid transfer protein, and the specific binding partners thereto, according to a predetermined protocol.

Other objects and advantages will become apparent to those skilled in the art from a review of the ensuing description which proceeds with reference to the following illustrate drawings.

DESCRIPTION OF THE DRAWINGS

FIG. 6A is a schematic drawing of the PLTP gene promoter-luciferase reporter construct. The promoter was PCR amplified from a BAC clone containing the genomic sequence for the human PLTP gene. FIG. 6B graphically presents the results calibrated in terms of luciferase activity, of a study where HepG2 cells were transfected with the PLTP promoter-luciferase reporter and were then treated with various doses of topotecan for 24 hrs. Cell extracts were harvested for the dual luciferase assay (Promega, Wis.). The relative luciferase activity has been normalized with the internal control renella luciferase activity cotransfected with the promoter reporter construct, to monitor transfection efficiency.

DETAILED DESCRIPTION OF THE INVENTION

In its broadest aspect the present invention relates to the regulation of phospholipid transfer protein (PLTP) gene expression by camptothecin and its derivatives and the effects on cholesterol metabolism. More particularly, the interaction of certain of the compounds of the camptothecin family with the expression of PLTP in HepG2 liver cells underlies the discovery that such chemical compounds and their structural cognates may represent a class of therapeutics with a broad range of applicability and action that has not been previously observed with lipid metabolism-related therapeutics in the past.

Figure 10:
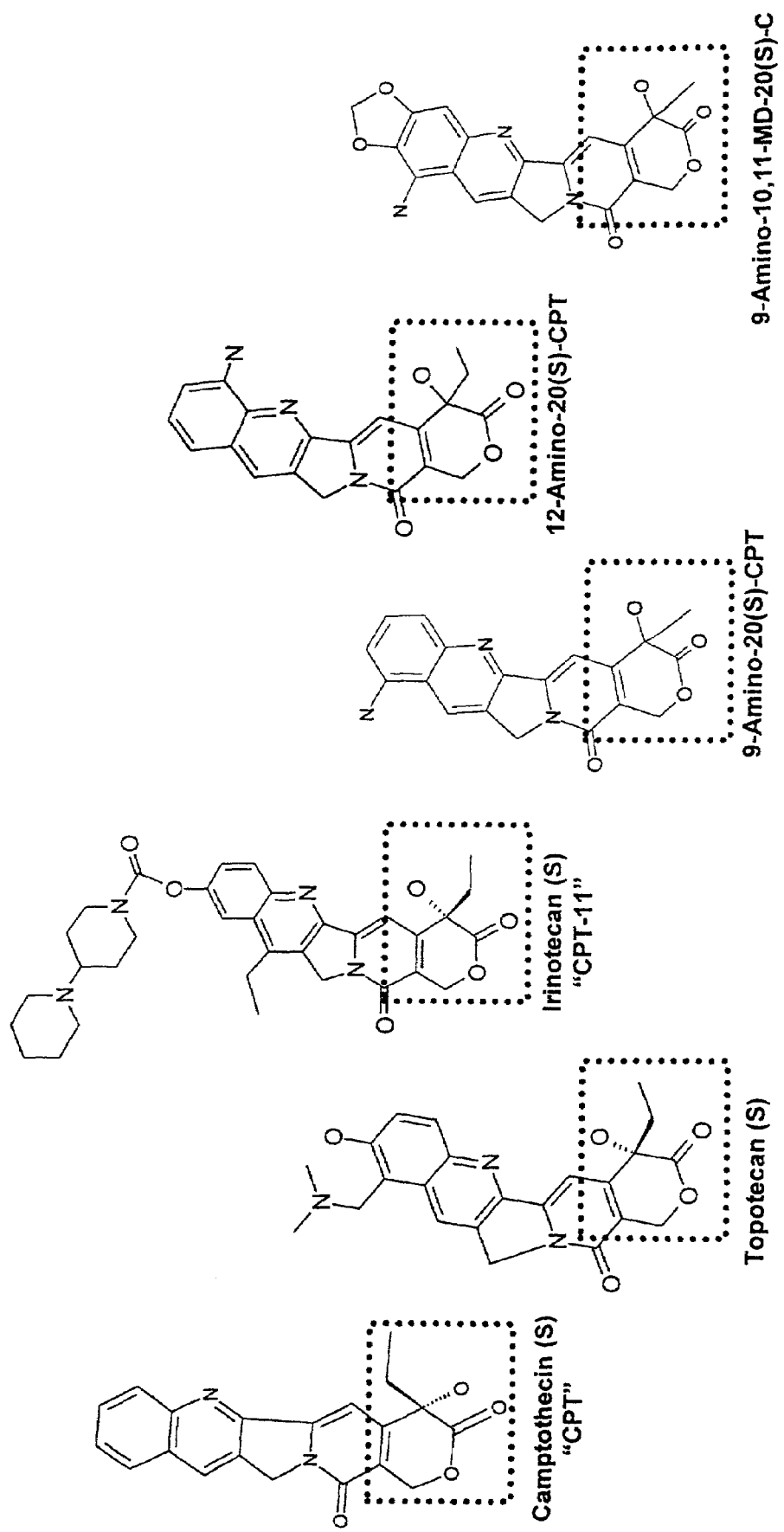
FIG. 10 depicts the structural formulas of several camptothecin derivatives, including camptothecin (CPT) and topotecan.

We have identified by DNA microarray the regulation of PLTP gene expression by camptothecin and its derivatives. The formulae of certain members of the camptothecin family are set forth in FIG. 10. Increases in PLTP gene expression are specifically induced by camptothecin and its derivatives which are active and capable of disrupting the function of topoisomerase I. Other cytotoxic anticancer compounds such as vinblastine failed to induced PLTP gene expression, thus suggesting that the induction may not be associated with apoptosis or programmed cell death triggered by these cytotoxic anticancer agents. The protracted course of induction of PLTP by camptothecin and its derivatives implicate the possibility that PLTP is regulated by the metabolites of camptothecin. Reports of endogenous synthetic intermediates in the plant camptotheca accuminata, such as the diterpenes, regulating genes in the cholesterol and the camptothecin biosynthetic pathway, further suggests that intermediate metabolites of camptothecin and its derivatives may regulate PLTP gene expression.

As part of the present invention, a promotor of the PLTP gene is prepared. The preparation of the PLTP promoter is described in detail below, and may accordingly be fused to the luciferase reporter construct. Such a promoter is shown herein to be activated by camptothecin and its derivatives, suggesting a transcriptional regulation of PLTP expression by these small molecules.

Expression Patterns:

Normal Tissues:

PLTP mRNA is expressed ubiquitously in various normal human tissues. The induction of PLTP expression by camptothecin and its derivatives seems to be cell-type specific, only in the human liver HepG2 cells, and not in any other cell types derived from various other tissues that have been examined to date.

PLTP is involved in reverse cholesterol transport, whereby PLTP mediates the transfer of cholesterol to high density lipoproteins (HDLs). The cholesterol loaded HDLs are taken up in the liver by the scavenger receptor class BI (SR BI). The cholesterol released from the endosome is secreted into bile acids for elimination. Transgenic mice that overexpressed PLTP has been demonstrated to have lower HDL cholesterol levels compared with normal mice, thus suggesting that PLTP can be an antiatherogenic factor in lowering plasma cholesterol levels. In contrast targeted disruption of PLTP function by homologous recombination showed that transgenic mice that lack PLTP and on a high fat diet may have increased propensity for the development of atherosclerosis.

These results all suggest that increased levels of PLTP is important in the regulation of cholesterol metabolism and is anti-atherogenic.

Cholesterol Metabolism and Lowering of Plasma Cholesterol Levels by Camptothecin and its Derivatives:

Results from the in vivo transgenic animal studies clearly demonstrate the beneficial role of increased PLTP levels in the plasma, which can facilitate the transfer of cholesterol to HDL, thus enhancing reverse cholesterol transport and the lowering of plasma cholesterol. Transgenic studies also showed that plasma from transgenic animals is much more efficient in preventing the accumulation of intracellular cholesterol in macrophages than plasma from wild-type mice.

The results set forth in the illustrative examples appearing later on herein, show for the first time that PLTP levels may be modulated pharmacologically by small molecules such as those of camptothecin and its derivatives. In view of the protracted time course or elapse in the induction of PLTP by camptothecin and its derivatives in the human liver carcinoma cells, it is not inconceivable that PLTP expression might be activated by the metabolites of these compounds.

Therefore, an aspect of the invention is to develop non-cytotoxic derivatives or metabolites of camptothecin that can be used as therapeutics for the lowering of plasma cholesterol. Unlike the statins, which inhibits HMG-coA reductase and thus de novo cholesterol biosynthesis, the non-cytotoxic camptothecin derivatives under development currently, act on a different pathway in cholesterol metabolism, namely by enhancing reverse cholesterol transport via HDL. In addition, the statins are therapeutically ineffective in patients with familial hypercholesterolemia, who are homozygously deficient for LDL-receptor. Two genetic diseases, the rare Tangier disease and the more common familial HDL deficiency, also may not benefit from statin therapy because Tangier disease is characterized by an extremely low concentration of circulating HDL and the accumulation of cholesteryl esters in tonsils, liver, spleen, and intestinal mucosa, mostly in macrophage foam cells. The genetic defects in both diseases are thought to be associated with mutations in the ABC1 gene, which belongs to the large ATP-binding cassette transporter family that transports many diverse substrates across membranes because of their channel-like topology. Patients with familial HDL deficiency exhibit a low concentration of HDL particles and an increased risk of coronary artery disease. A common explanation for the cardioprotective effect of HDL is the major role it plays in reverse cholesterol transport. The development of agents that raise PLTP levels and subsequently the pre-HDL levels will be an important therapeutic intervention for these patients for which there is currently no effective therapeutic strategy.

As mentioned earlier, an aspect of the invention extends to a method for the identification of agents that may serve to control cholesterol metabolism and that may consequently, be developed as pharmaceutical compositions and that may be administered to treat the conditions that result from abnormalities or dysfunctions in a host or patient. The method may be practiced with a screening assay where a multitude of possible small molecules, etc., may be examined on a high throughput basis. Such an assay would comprise an appropriate cellular substrate, the PLTP promoter with a reporter or label, and directions for use.

The following is a description of the promotor construct that can be used in a screening assay in accordance with the invention, and an exemplary protocol.

Materials:

Human: full length coding sequence of PLTP in pCDNA3.1; promoter sequence of PLTP in a reporter plasmid; fusion construct of PLTP with GST in the pGEX4T-1 vector. Such a vector may be constructed as follows. Accordingly, the expression vector of PLTP is prepared with its full length cDNA inserted into pcDNA3.1 (Invitrogen) under the control of the CMV promoter. The vector also contains the selectable neomycin resistance marker gene. The vector as prepared may then be used in accordance with the invention to screen for small molecules and other potential modulators of PLTP expression and consequent modulation of cholesterol processing.

For transfection, approximately $1.0\times10^6$ HepG2 cells may be plated in 100 mm dishes and then may be transfected with either the expression plasmid containing the PLTP gene or pcDNA3.1 (empty vector) using Lipofectamine (Life Technologies, Inc., MD) according to the manufacturer's specification. The liposome DNA precipitate is washed out approximately 3 hr after transfection and cells are further cultured for about 48 hrs. Cells are then subcultured and plated in duplicate in 100 mm dishes at $1.0\times10^5$ cells for G418 selection. We have previously determined the sensitivity of HepG2 cells to G418 and will conduct the selection at approximately 800 μg/ml of drug. G418 resistant clones will be isolated and expanded individually for characterization of PLTP overexpression by Northern analysis. Total RNA will be isolated from the transfectants using TRIZOL Reagent (Life Technologies, Inc.) and Northern analysis will be performed using $^{32}P$-labeled full-length PLTP cDNA probe to identify transfectants with elevated PLTP expression.

Next, certain of the clones that exhibit PLTP expression could be contacted with the candidate agent to observe any changes in expression level. One could use either the clonogenic survival assay or the MTT assay. For the clonogenic assay, approximately 300 cells could be plated in the 60 mm tissue culture dishes followed by incubation with various drugs for dose response experiments. Alternatively, 1.0×10³ cells could be plated in 96 well dishes the day before, and dose-response experiments will be conducted with the agent candidates as described with reference to camptothecin and topotecan in the examples below. The MTT assay is performed 72 hrs post-treatment. Results from such experiments would make it possible to determine whether particular candidates exhibit the desired effect for use in cholesterol control.

Antibodies

Antibodies to PLTP are useful as they may serve in drug assays as well as to participate in the modulation of PLTP activity. Antibodies may be raised in a variety of well known ways, and the present invention extends and includes such well known techiques within its scope. A particular protocol is presented as follows. Antiserum is generated in New Zealand white rabbits according to standard procedures (19) at the Pocono Rabbit Farm (Canadensis, Pa.). Purified PLTP protein such as may be prepared with the vector described above, may be used as antigen. A desirable and useful antibody preparation is one that is affinity purified with the antigen. In such instance, the IgG fraction of the antiserum will be isolated using DEAE-Affi-Gel blue followed by affinity purification of the anti-PLTP antibody using nitrocellulose-bound PLTP protein as an affinity adsorbent. The specificity of the antibody will be assessed by immunoprecipitation and immunoblot analyses. Preimmune IgG will be used to monitor nonspecific effects.

The following examples are presented by way of illustration and not by way of limitation.

EXAMPLE 1

Pharmacological Response of HePG2 Cells to Topotecan by DNA Microarray

We have used DNA microarray to monitor the expression profiles of cells in response to anticancer drug treatments, and also comparing these profiles to those obtained from cancer cells that have been selected for resistance to the corresponding agents. We have recently examined the pharmacological response of cancer cells to topotecan, a semi-synthetic derivative of camptothecin, in the human hepatocellular blastoma HepG2 cells. In these studies, time-course and dose-response experiments with topotecan were performed as follows.

The HepG2 cells were either transiently treated with 500 nM of topotecan for various times (1–24 hrs), or with various doses of topotecan (1–1000 nM) for 24 hrs. Total RNA prepared from these cells was used to synthesize 33P-labeled cDNAs by reverse transcription followed by hybridization to the human GeneFilter™ GF211 from Research Genetics Inc. (Huntsville, Ala.). These microarrays are 5×7 cm Nylon membrane containing 4,133 spots corresponding to functionally known human genes. The array also contains 576 spots of total genomic DNA, which serve as reference points for the image analysis software, Pathway™ (Research Genetics Inc.), for normalization purposes and for verifying the homogeneity of the hybridization. Hybridized filters were washed and then exposed to phosphorimage screens for the appropriate amount of time, followed by scanning on the Molecular Dynamics Storm Phosphorimager. The scanned images were processed and analyzed on the Pathways™ software. Tab delimited files generated from Pathways™ were imported into Microsoft Excel® for sorting by fold changes and intensity levels (radioactivity, cpm). Based on our experience, we only include genes that exhibit greater than two fold changes in expression (up- or downregulation) and have differences in intensity levels greater than 1,000 cpm, in the expression profiles. In addition, data points that do not align correctly were also excluded from the profiles. These results were then further subjected to hierarchical clustering analysis using the software developed by Eisen et al. (1). The results are displayed using the accompanying TreeView software and are presented in FIG. 1 as a dentogram showing clusters of gene expression based on their similarity in the patterns of expression.

Figure 1:
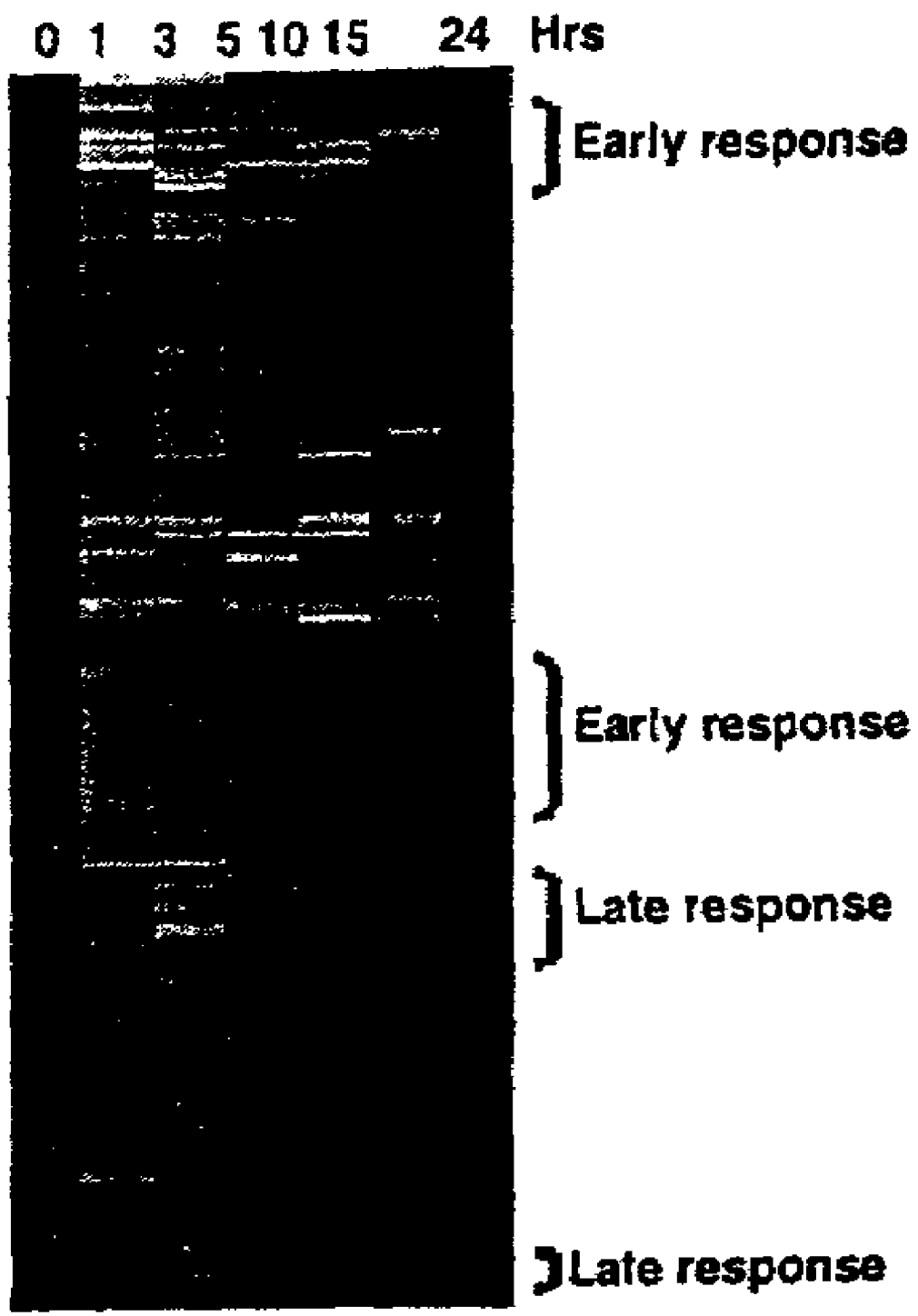
FIG. 1 is a DNA microarray presenting expression profiling of topotecan induced HepG2 cells. HepG2 cells were treated with 500 nM of topotecan in time course study for the indicated time points in the figure. RNAs were isolated, labeled and hybridized to the array. Scan image were analyzed using the Pathway and the Cluster softwares. The results of cluster analysis are shown in TreeView. Transition of color to red indicates the upregulation, and to green is the downregulation of gene expression.
Figure 2:
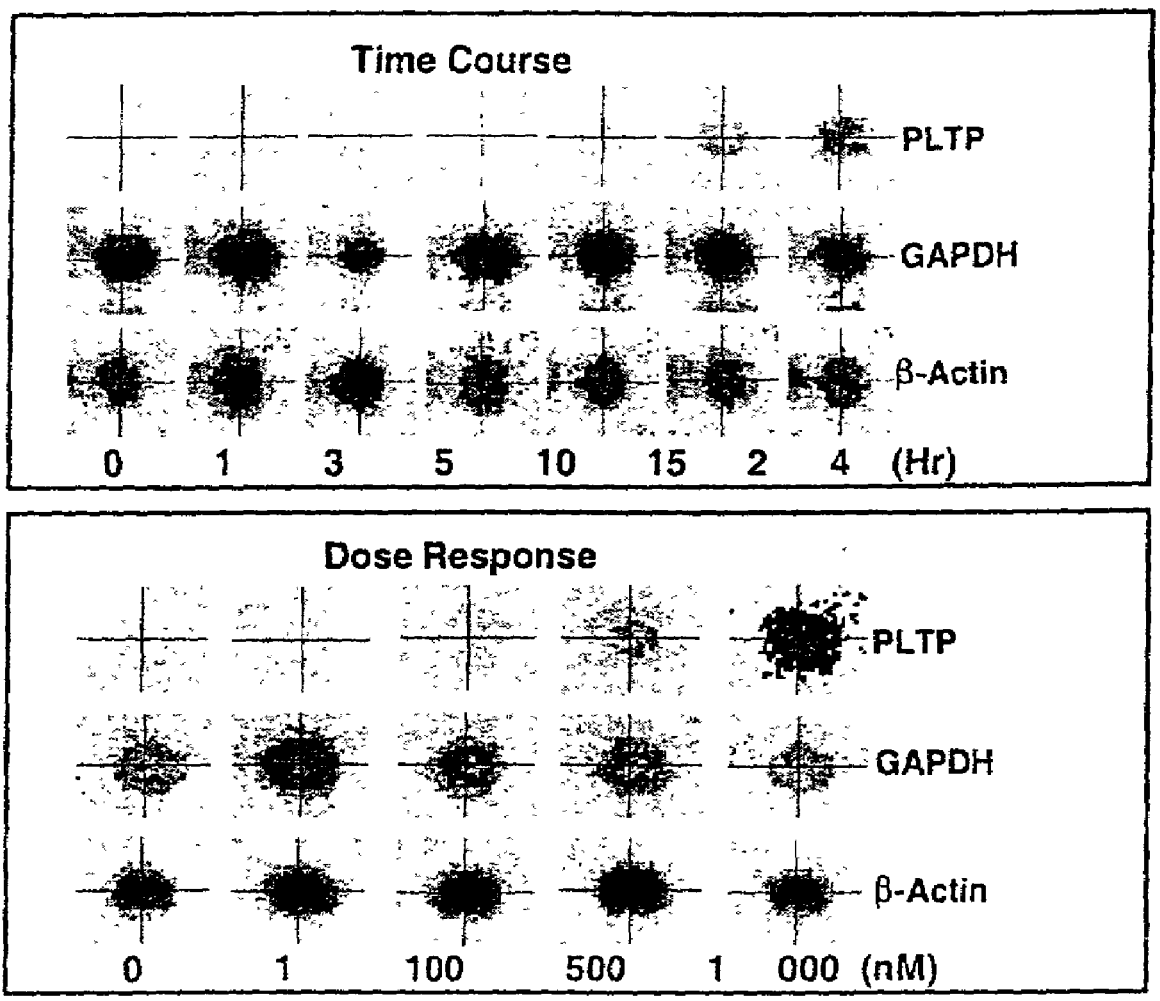
FIG. 2 is a scanned image of the PLTP gene induced by topotecan. HepG2 cells were treated with topotecan in time-course and dose response studies. The microarrays were exposed to phosphorimage screen and the scanned images were analyzed with the Pathway software. Enlarged scanned images for the induction of PLTP gene with time and dose are shown. The controls GAPDH and -actin exhibit no significant variations in the experiments.
Figure 3:
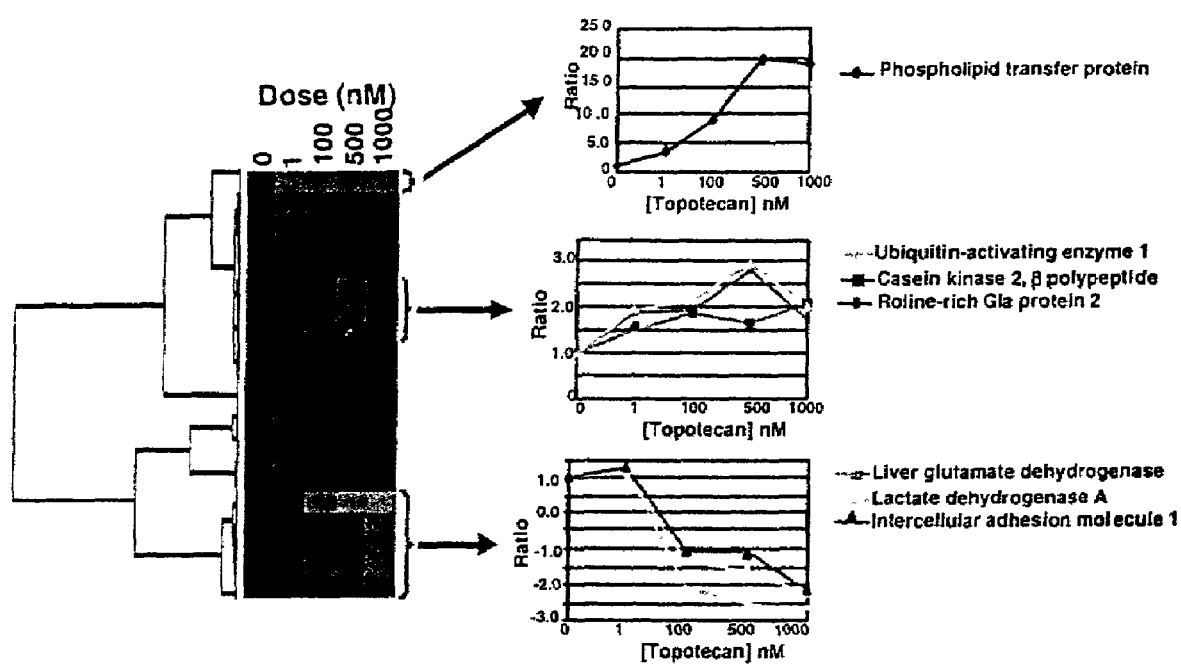
FIG. 3 is a DNA microarray presenting expression profiling of topotecan induced HepG2 cells. HepG2 cells were treated with various concentrations of topotecan. RNAs were isolated, labeled and hybridized to the array. Scan images were analyzed using the Pathway and the Cluster softwares. The results of cluster analysis are shown in TreeView. A representative set of genes with altered expression was plotted in the line graphs. Transition of color to red indicates the upregulation, and to green is the downregulation of gene expression.

FIG. 1 showed the TreeView image from a hierarchical clustering analysis of the time course study. Distinct changes in gene expression were observed with topotecan treatment. Temporal changes in gene expression were observed, resulting in clusters of genes whose onset of induction was either early or late in response to topotecan. The phospholipid transfer protein (PLTP) gene was the most strongly induced, up to approximately 20-fold after 24 hrs of exposure (FIG. 2, top panel) while control genes such as -actin and glyceraldehyde phosphate dehydrogenase (GAPDH) showed no alterations in their expression. In addition, the induction of PLTP was delayed as the onset of its expression was not observed until 10–15 hr after exposure to topotecan (FIG. 2). Induction of PLTP was also observed in dose response studies whereby its expression was elevated in a dose dependent manner in response to topotecan treatment (FIG. 2, bottom panel, and FIG. 3, top insert). Changes in the expression of other genes were also observed including the lactate and the glutamate dehydrogenases, casein kinase 2, and ubiquitin activating enzyme E1 and others (FIG. 3, inserts) in response to topotecan.

EXAMPLE 2

In previous studies with doxorubicin, we found that some of the genes that are induced to high levels of expression by doxorubicin are also targeted for overexpression in cells that were selected for resistance to doxorubicin, thus suggesting these genes may contribute to increased drug resistance (2). Since PLTP expression was the most strongly induced by topotecan in these experiments, we further investigated whether PLTP expression may be associated with drug resistance. We first examined topotecan-induced PLTP expression in an independent dose response study by Northern blot analysis. Our results showed that PLTP was induced by topotecan and its expression was elevated with increasing doses of topotecan (FIG. 4), consistent with those observed in the microarray studies. A biphasic response was observed in PLTP gene expression. A dose dependent induction of PLTP was observed, but was reversed at 1 μM of topotecan. This may be a result of the inhibition of transcription by topotecan at the higher dosage.

EXAMPLE 3

To determine whether the induction of PLTP expression is topotecan specific, we evaluated the effects of camptothecin and some of its derivatives, and compared them against some protoberberines, which are a new class of organic cations that are dual poisons of topoisomerases I and II (3–5). Berberine is an isoquinoline plant alkaloid. Plant extracts containing berberine have been used widely in Chinese and Indian folk medicine for many years, and they demonstrate weak antitumor activity in mice (6). Several of the protoberberine analogues have already been demonstrated to have significant cytotoxicity against cultured tumor cell lines (3,4). The results are set forth in Table 1, below.

TABLE 1

Camptothecin derivatives and the protoberberines.

| Camptothecin & derivatives | Cytotoxicity | Protoberberines | Cytotoxicity |
|---|---|---|---|
| Camptothecin (CPT) | Active | DM-II-32 | Weakly active |
| 9-NH2-CPT(S) | Active | DM-I-159 | Weakly active |
| Irinotecan (CPT-11) | Inactive prodrug | DM-I-170 | Weakly active |
| 9-NH2-10,11-MD-CPT(S) | Active | YYN-I-40 | Weakly active |
| 9-NH2-10,11-MD-CPT(R) | Inactive | YYN-I-74 | Active |

Figure 5:
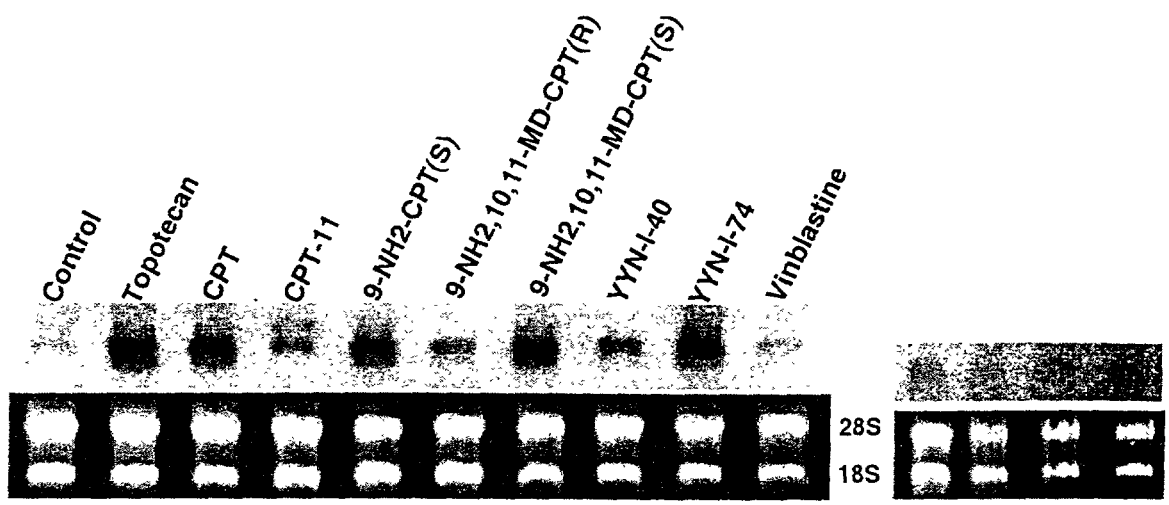
FIG. 5 is a gel demonstrating the induction of PLTP expression by camptothecin and its derivatives and protoberberines. HepG2 cells were treated with the indicated drugs (500 nM) for 24 hrs. RNAs were then harvested and fractionated on agarose gel and then transferred to nitrocellulose filters for hybridization with a full length PLTP cDNA probe.

Referring to Table 1, the results showed that camptothecin and its derivatives were generally more effective than the protoberberines tested. The results also demonstrated that, in addition to topotecan, PLTP expression can also be induced by camptothecin, 9-NH2-CPT(S), 9-NH2-10,11-MD-CPT(S), and the protoberberine YYN-I-74 (FIG. 5). Furthermore, results with the 9-NH2-10,11-MD-CPT(S) and 9-NH2-10,11-MD-CPT(R) enantiomers clearly indicate that the induction of PLTP is linked to its topoisomerase I inhibitory activity. The inactive prodrug CPT-11 also failed to activate PLTP expression, presumably due to the inability of HepG2 cells to hydrolyse and convert the prodrug into its active form in culture. Since the onset of PLTP expression is delayed by 10–15 hours following topotecan induction, it was speculated that that its activation may be associated with the cytotoxicity of the drug. However, this possibility is excluded because treatment with the anti-microtubule drug vinblastine, which is also a cytotoxic anticancer agent, did not induce PLTP expression. The inactive or weakly active derivatives of camptothecin or the protoberberines all failed to induce PLTP expression.

EXAMPLE 4

Figure 4:
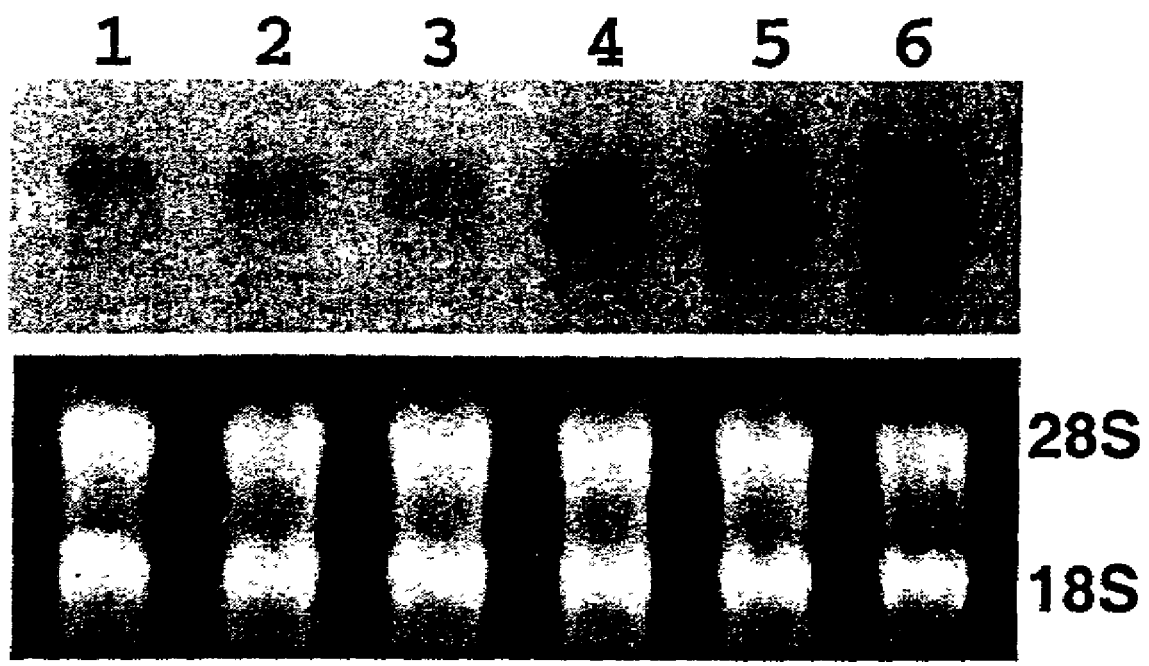
FIG. 4 is a gel that demonstrates the induction of PLTP by topotecan. Dose response induction of PLTP was performed in HepG2 cells for 24 hrs. RNAs isolated were separated on agarose gel and then transferred to nitrocellulose filters for hybridization with a labeled full-length PLTP cDNA probe. Ethidium bromide stained gel showed equal loading of the RNA samples. Lane 1, control (untreated); 2, 1 nM; 3, 20 nM; 4, 100 nM; 5, 500 nM; and 6, 1,000 nM topotecan expression. A dose dependent induction of PLTP was observed, but was reversed at 1 µM of topotecan. This may be a result of the inhibition of transcription by topotecan at the higher dosage.
Figure 6:
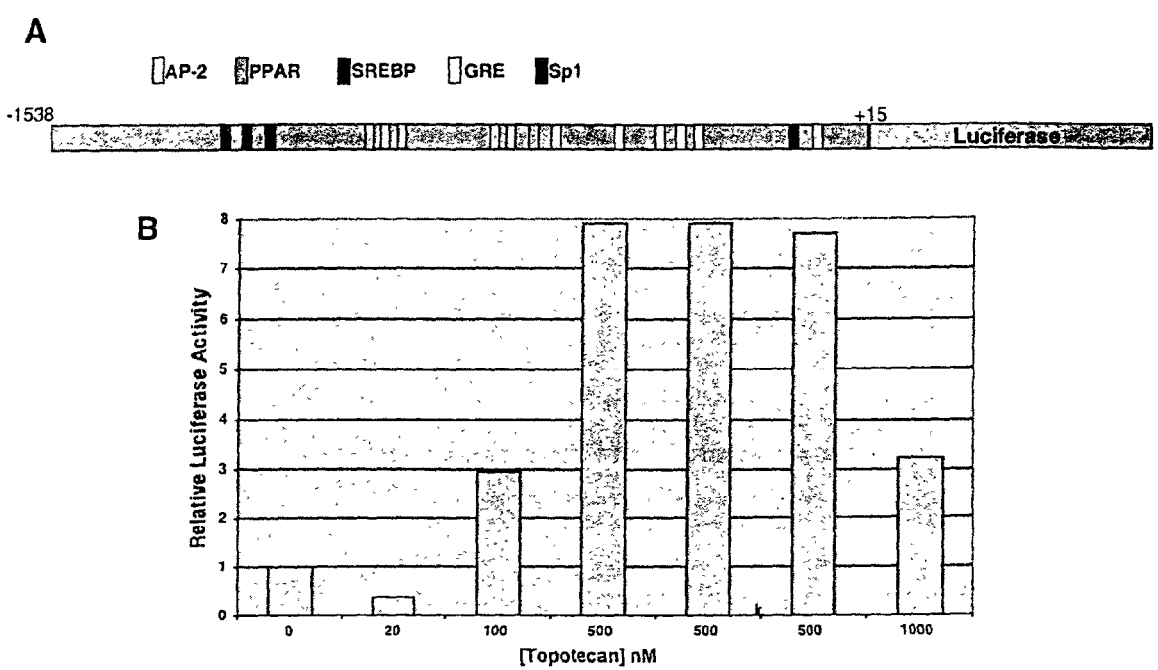
FIGS. 6A and 6B depict the transactivation of the PLTP promoter by topotecan.
FIG. 6C is the DNA sequence of the PLTP gene construct inserted into the PLTP promoter depicted and described in FIG. 6A.

We also determined whether induction of PLTP gene expression by topotecan is transcriptionally activated. Approximately 1.5 kb of the PLTP promoter sequence was obtained by the polymerase chain reaction (PCR) amplification of a human BAC clone (RP3-337018) containing the genomic sequence of PLTP. The PCR product consisting of the promoter region was sequenced verified and then subcloned into a luciferase reporter vector pGL2-Basic vector (Promega, Wis.) (FIG. 6A). The PLTP promoter-reporter construct was cotransfected with the renella luciferase expression vector, as internal control to monitor transfection efficiency, into HepG2 cells. The cells were then treated with various doses of topotecan for 24 hrs and cells extracts were harvested for the dual luciferase assay (Promega) at the end of drug exposure. Our results showed that the PLTP promoter can be transactivated by topotecan dose-dependently (FIG. 6B). At 1 µM topotecan, inhibition of the promoter activity was observed due to transcriptional inhibition, which is consistent with our results in the dose-response induction of PLTP expression by Northern blot analysis (FIG. 4). These results suggest that the induction of PLTP expression by topotecan is transcriptionally activated.

EXAMPLE 5

Figure 7:
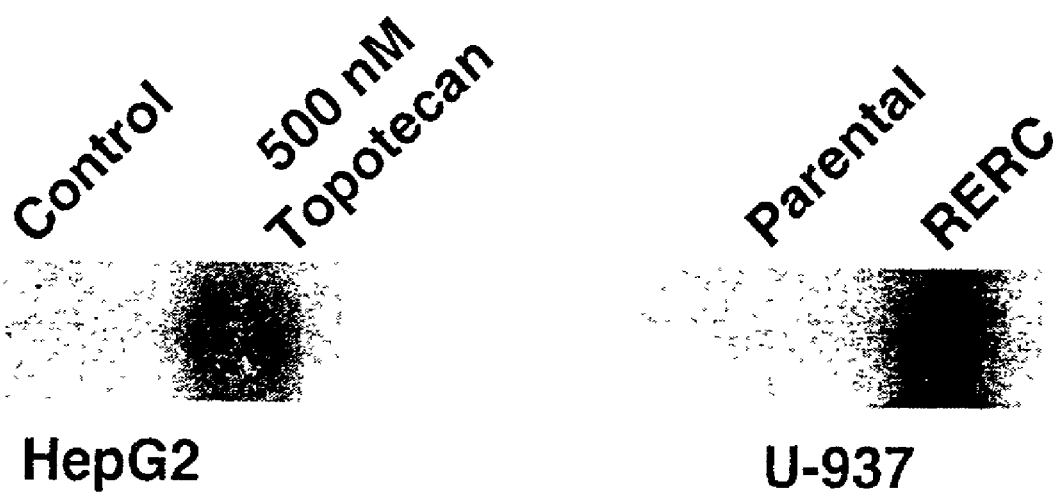
FIG. 7 presents the results of Northern blot analysis of expression of PLTP gene in a camptothecin resistant cell line. Northern blot analysis of PLTP gene expression was performed with the U-937 cells and its subline RERC, which was sequentially selected for resistance to camptothecin and etoposide. HepG2 cells treated with 500 nM of topotecan for 24 hr was used as a positive control.

To substantiate the hypothesis that PLTP might play a role in the resistance to camptothecin and its derivatives, the expression of PLTP was examined in a U-937 leukemic subline, denoted RERC, which was selected sequentially for resistance to camptothecin and etoposide (7), by Northern blot analysis. The results are set forth in FIG. 7, and showed that the PLTP gene is markedly overexpressed in the drug-resistant RERC cells, thus suggesting that elevated PLTP levels may play a role in the resistance to camptothecin in these cells.

Figure 8:
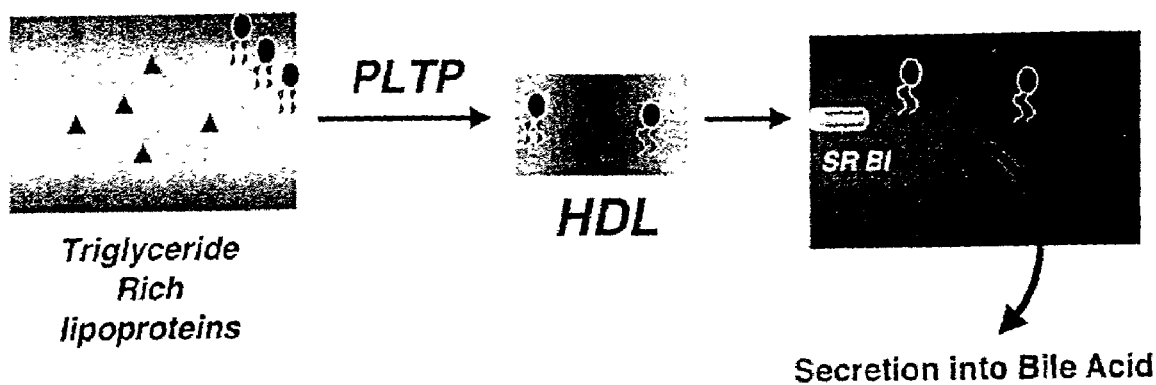
FIG. 8 schematically depicts the role of PLTP in reverse cholesterol transport. PLTP is involved in reverse cholesterol transport by transferring phospholipids and cholesterol from triglycerides-rich lipoproteins into HDL. The lipids loaded-HDL binds to the scavenger receptor B1 (SR-B1) and is internalized. The cholesterol released from the endosome is then secreted into bile acid.

The alteration of PLTP gene expression is interesting because PLTP is one of the major serum proteins that facilitates the transfer of cholesterol and phospholipids into high density lipoproteins (HDL) (8–10). The human PLTP gene contains 16 exons, spanning approximately 13 kb on the long arm of chromosome 20 (11,12). The cDNA is 1750 base pairs long and encodes a 476 amino acid protein (See 13 and U.S. Pat. No. 5,622,843). The molecular weight of purified PLTP on SDS PAGE is approximately 81 kDa, much larger than the protein mass predicted from the cDNA. PLTP has an important role in determining HDL levels and speciation by reverse cholesterol transport (8). PLTP can transfer free cholesterol from triglyceride-rich lipoproteins (TRL) into HDL (FIG. 8), and this activity is almost abolished in PLTP knockout mice (14). Therefore, raising PLTP levels in accordance with an aspect of the invention, by using pharmacological agents such as those of camptothecin and its derivatives, as well as other non-cytotoxic small molecules derivatives of camptothecin, can lead to an increase in the potentially anti-atherogenic pre-HDL particles. The lipids or cholesterol loaded-HDL is subsequently taken up by the liver via the scavenger receptor B1 (SR-B1), a selective mechanism of uptake of HDL in the liver (FIG. 8).

It has been demonstrated that a high cholesterol diet increases PLTP activity and PLTP mRNA in mice (15,16). The crystal structure of the bacterial permeability increasing protein, reveals that proteins in this family including PLTP, contain intrinsic lipid binding sites and appear to act as carrier proteins that shuttle between lipoproteins to redistribute lipids (17,18). More importantly, cholesterol has been shown to be a substrate of PLTP (9,10). Like cholesterol, topotecan also stimulates PLTP gene expression as shown in the data presented in FIGS. 2-6 and discussed above. Therefore, we speculate that topotecan may be a substrate for PLTP and mimics cholesterol in upregulating PLTP gene expression.

Figure 9:
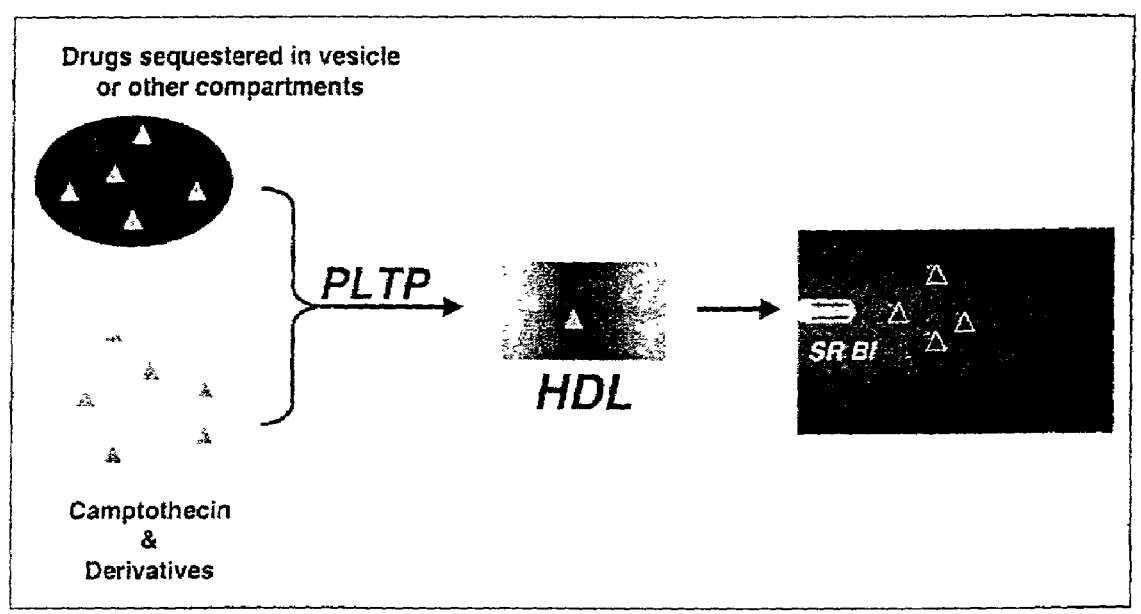
FIG. 9 is a schematic illustration of PLTP-mediated resistance to camptothecin and its derivatives. Treatment with the camptothecin family of drugs induces PLTP gene expression. The increased levels of PLTP in the serum may enhance the binding and shuttling of camptothecin and its derivatives to HDL, which will be taken up into the liver via the SR BI receptor and degraded. The drugs released from the degraded HDL presumably will be metabolized. Therefore, elevated levels of PLTP induced by camptothecin and its derivatives may enhance their metabolism via the reverse cholesterol transport pathway and increase drug resistance.

These results also suggest that topotecan may induce its own resistance during chemotherapy by activating PLTP gene expression. The increased levels of PLTP may enhance the transfer of topotecan and other camptothecin derivatives to HDL, which in turn is taken up by the liver via SR-B1 and metabolized, thus leading to increased topotecan resistance (FIG. 9).

Alternatively, because of the delayed induction of PLTP by topotecan, it is possible that increased levels of PLTP may be associated with the induction of apoptosis, triggered by topotecan-mediated DNA damage. We speculate that increased expression of PLTP may have anti-apoptotic effects thus affecting cellular sensitivity to the camptothecin family of agents.

EXAMPLE 6

Figure 11:
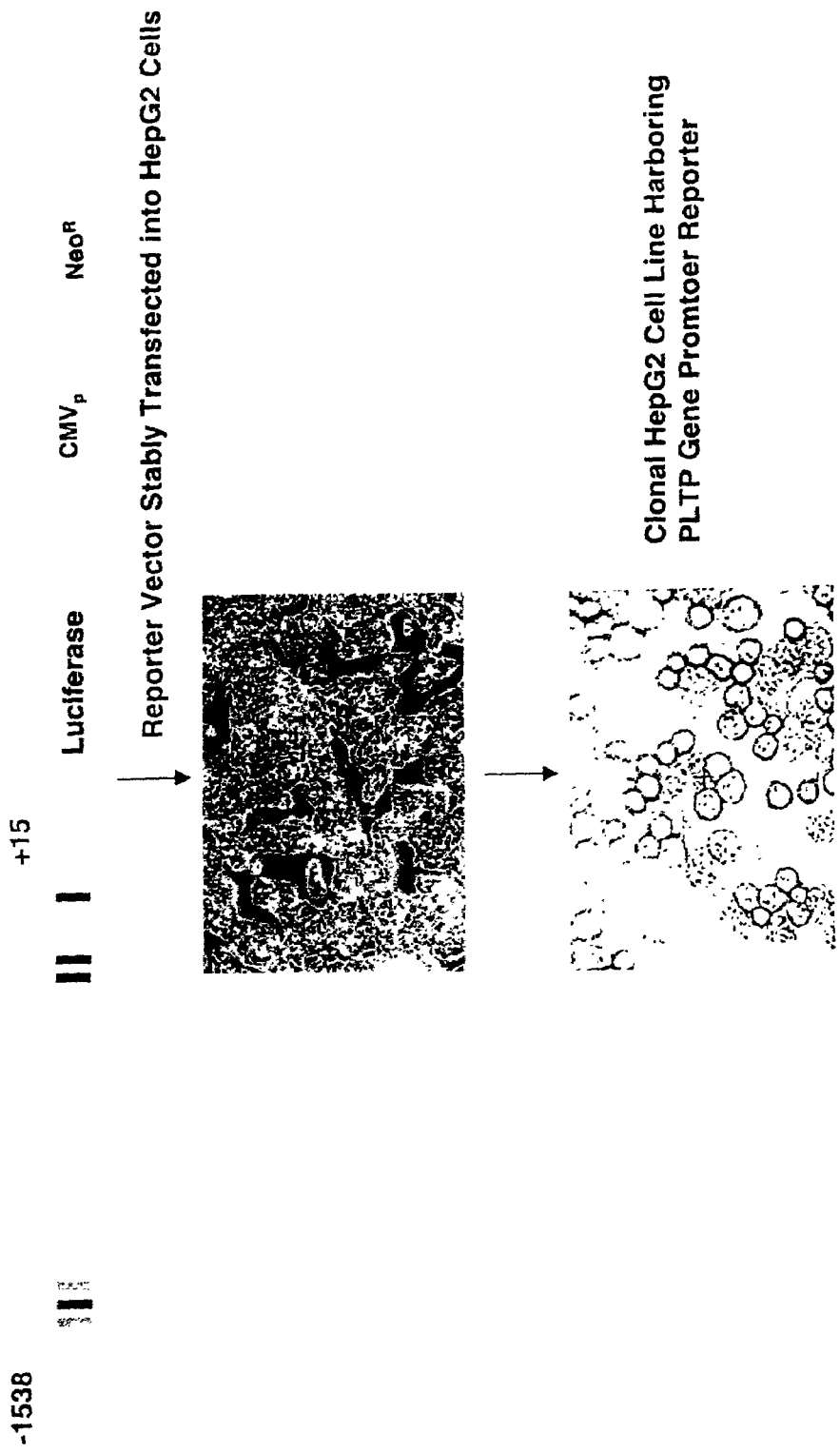
FIG. 11 is a schematic drawing of the promoter of the phospholipid transfer protein (PLTP) gene. A 1.6 kb fragment of the PLTP gene promoter derived from a BAC clone was PCR amplified and then subcloned into a modified pXP1 luciferase reporter plasmid vector. The modified vector contained the neomycin resistance marker gene.

The luciferase reporter plasmid was constructed by cloning the PLTP promoter derived from a BAC clone into the pXP2 luciferase reporter vector. A neomycin selectable marker gene driven by the CMV early promoter was further subcloned into the PLTP-luciferase reporter plasmid (FIG. 11).

Approximately 10 μg of the PLTP-luciferase reporter plasmid was transfected using lipofectamine into HepG2 cells for about 4 hrs. Cells were washed and then further cultured and selected in the presence of 1.6 mg/ml of G418 for neomycin resistance. Media were changed every 3 days with fresh G418 added at the above concentration. Approximately 14 days later, colonies that emerged from the selection were picked using cloning cylinders and the clones were transferred to 24-well cluster dishes for further culturing and selection.

At confluence, cells were next transferred to 12-well dishes and aliquots were also transferred to 24-well dishes for screening with topotecan for induction of the PLTP promoter activity. Luciferase assay was performed using a standard luciferase assay kit from Promega. Clones exhibited positive response to topotecan induction were identified and further expanded.

Through this process, Clone #1, now designated as HepG2/PLTPpLuc, was identified. This clone responded to TPA induction robustly, mimicking those observed with the endogenous gene induced by topotecan.

Figure 12:
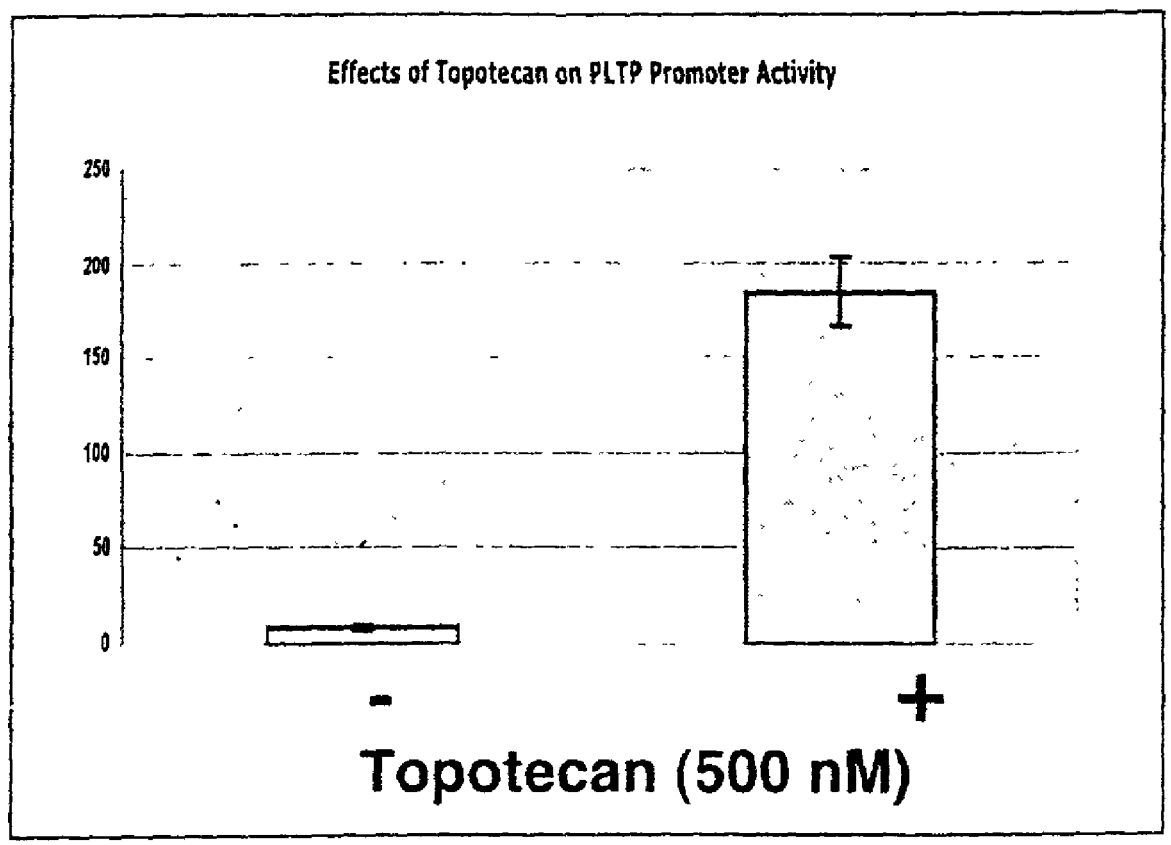
FIG. 12 demonstrates the induction of PLTP promoter by topotecan in a PLTP promoter/reporter transgenic cell line. HepG2 cells were permanently transfected with the construct shown in FIG. 11, and selected for resistance to G418, an aminoglycoside antibiotic. Clone 1, a G418 resistant cell line isolated from the selection, designated HepG2/PLTP$_p$Luc, was utilized for testing the effect of topotecan on induction of PLTP promoter activity. The transfectant cell line, HepG2/PLTP$_p$Luc, was treated with topotecan (500 nM) for approximately 24 hours. Cell extracts were obtained at the end of incubation and the luciferase assay was performed with them. The luciferase activity of the topotecan treated cells (+) was plotted relative to the control (−).
Figure 13:
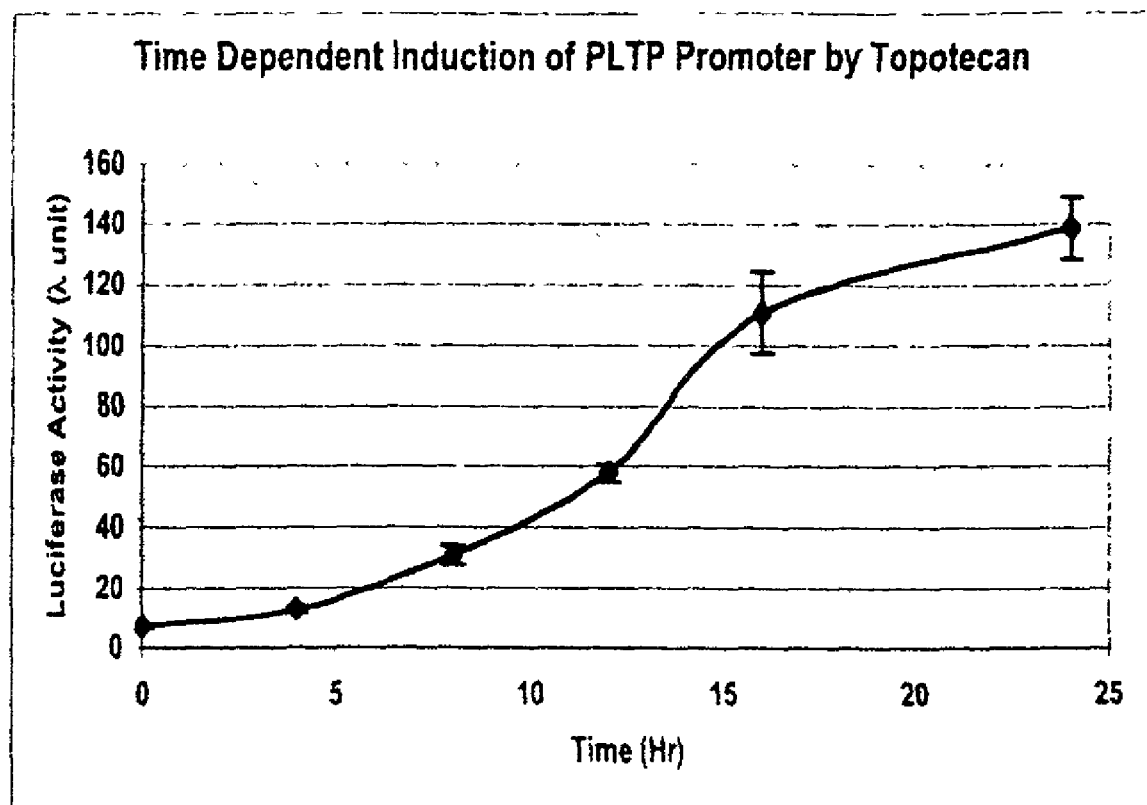
FIG. 13 illustrates the time course analysis of induction of PLTP promoter activity by topotecan in HepG2/PLTP$_p$Luc cells. The HepG2/PLTP$_p$Luc cells were treated with 500 nM of topotecan. Cell extracts were obtained at various time points following treatment with topotecan (0, 4, 8, 12, 16, and 24 hours) and assayed for luciferase activity, which was plotted as a function of time. Close to 20 fold maximal induction was achieved at 24 hours.
Figure 14:
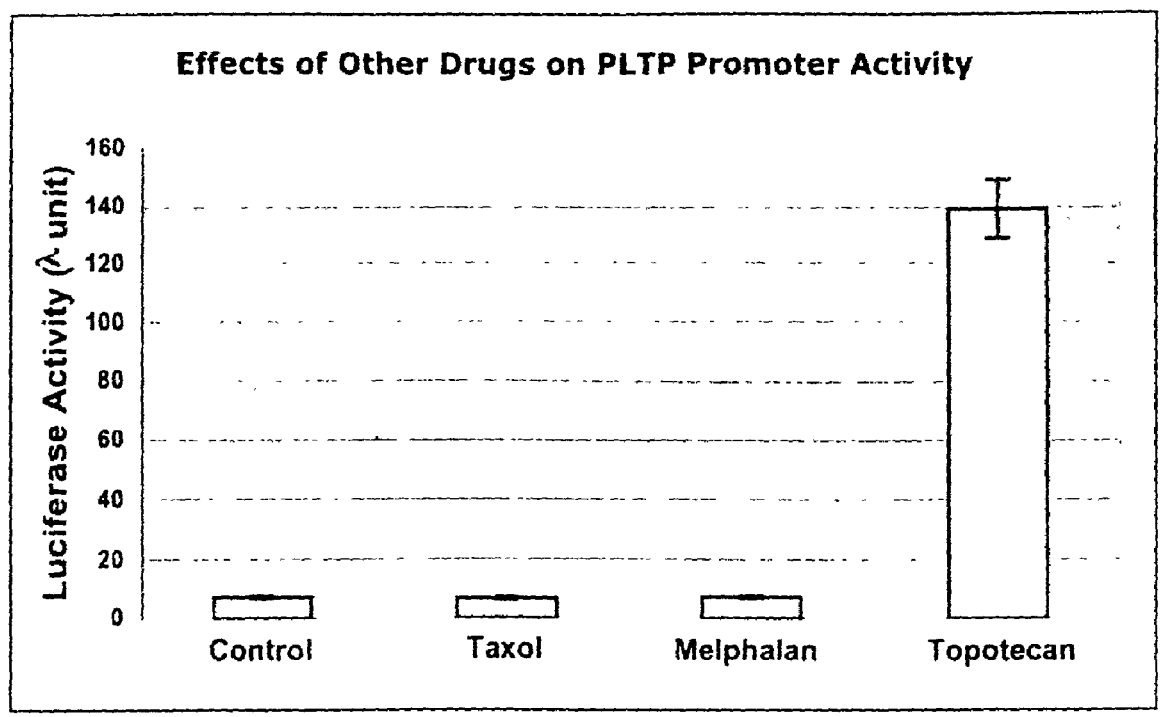
FIG. 14 demonstrates the specificity of induction of PLTP promoter activity by anticancer drugs in HepG2/PLTP$_p$Luc cells. The HepG2/PLTP$_p$Luc cells were treated with either topotecan, taxol, or melphalan for 24 hours. Cell extracts were then obtained for the luciferase assay. The induction of the PLTP promoter activity is specific for topotecan. No significant stimulation of PLTP promoter activity was observed with either taxol or melphalan.

Upon treatment with topotecan, this clonal cell line HepG2/PLTP$_p$Luc, conferred approximately 20-fold induction of the PLTP promoter activity (FIG. 12), which correlates well with the induction of the endogenous gene in HepG2 cells treated with topotecan. Time course analysis of the induction indicated a time-dependent increase in the promoter activity induced by topotecan and achieving close to maximal induction of 20-fold at 24 hr (FIG. 13). The induction of the PLTP promoter activity is specific for topotecan and no significant stimulation was observed for either taxol or melphalan (FIG. 14).

The results shown here demonstrated that the HepG2 cell line, which was stably transfected with a plasmid vector containing the promoter of PLTP gene fused to the luciferase reporter gene, selected in G418, is responsive to stimulation specifically by topotecan but not by either taxol or melphalan. Induction of the PLTP gene promoter activity by topotecan is time-dependent that seemed to peak by 24 hrs after drug exposure. As demonstrated herein, the HepG2 cell line and a clone of this cell line, designated HepG2/PLTP$_p$ Luc, are suitable as a vehicles for high-throughput screening for agents that can induce PLTP gene expression.

The following is a list of documents related to the above disclosure and particularly to the experimental procedures and discussions. These documents, and all others cited above, should be considered as incorporated by reference in their entirety.

(1) Eisen, M. B., Spellman, P. T., Brown, P. O., and Botstein, D. Cluster analysis and display of genome-wide expression patterns. Proc. Natl. Acad. Sci. USA, 95:14863–14868, 1998.

(2) Kudoh, K., Ramanna, M., Ravatn, R. Elkahloun, A. G., Bittner, M. L., Meltzer, P. S., Trent, J. M., Dalton, W. S., and Chin, K.-V. "Analysis of the Mechanisms of Drug Resistance in Cancer by cDNA Microarray", Cancer Res., 60:4161–4166, 2000.

(3) Makhey, D., Gatto, B., Yu, C., Liu, A., Liu, L. F., and LaVoie, E. J. Protoberberine alkaloids and related compounds as dual inhibitors of mammalian topoisomerase I and II. Med. Chem. Res. 5:1–12, 1995.

(4) Gatto, B., Sanders, M. M., Yu, C., Wu, H. Y., Makhey, D., LaVoie, E. J., and Liu, L. F. Identification of topoisomerase I as the cytotoxic target of the protoberberine alkaloid coralyne. Cancer Res. 56:2795–2800, 1996.

(5) Makhey, D., Gatto, B., Yu, C., Liu, A., Liu, L. F., and LaVoie, E. J. Coralyne and related compounds as mammalian topoisomerase I and topoisomerase II poisons. Bioorg. Med. Chem. 4:781–91, 1996.

(6) Suffness, M., and Cordell, G. A. Antitumor alkaloids. In: The Alkaloids (Ed. Brossi, A.), Vol. 28:95–181. Academic Press, Orlando, Fla., 1986.

(7) Saleem, A., Ibrahim, N., Patel, M., Li, X. G., Gupta, E., Mendoza, J., Pantazis, P., and Rubin, E. H. Mechanisms of resistance in a human cell line exposed to sequential topoisomerase poisoning. Cancer Res. 57:5100–106, 1997.

(8) Bruce, C., Chouinard, R. A. Jr., and Tall, A. R. Plasma lipid transfer proteins, high density lipoproteins, and reverse cholesterol transport. Annu. Rev. Nutr. 18: 297–330, 1998.

(9) Nishida, H. I., and Nishida, T. Phospholipid transfer protein mediates transfer of not only phosphatidylcholine but also cholesterol from phosphatidylcholine-cholesterol vesicles to high density lipoproteins. J. Biol. Chem. 272:6959–6964, 1997.

(10) Wolfbauer, G., Albers, J. J., and Oram, J. F. Phospholipid transfer protein enhances removal of cellular cholesterol and phospholipids by high-density lipoprotein apolipoproteins. Biochim. Biophys. Acta. 1439:65–76, 1999.

(11) Tu, A. Y., Deeb, S. S., Iwasaki, L., Day, J. R., and Albers, J. J. Nucleotide organization of human phospholipid transfer protein gene. Biochem. Biophys. Res. Commun. 1207:552 558, 1995.

(12) Whitmore, T. E., Day, J. R., and Albers, J. J. Localization of the human phospholipid transfer protein gene to chromosome 20q12–q13.1. Genomics 28:599–600, 1995.

(13) Day, J. R., Albers, J. J., Lofton-Day, C. E., Gilbert, T. L., Ching, A. F., Grant, F. J., O'Hara, P. J., Marcovina, S. M., and Adolphson, J. L. Complete cDNA encoding human phospholipid transfer protein from human endothelial cells. J. Biol. Chem., 269:9388 9391, 1994.

(14) Jiang, X.-c., Bruce, C., Mar, J., Lin, M., Ji, Y., Francone, O. L., Tall, A. R. Targeted mutation of plasma phospholipid transfer protein gene markedly reduces high-density lipoprotein levels. J. Clin. Invest. 103:907–914, 1999.

(15) Tu, A. Y., Paigen, B., Wolfbauer, G., Cheung, M. C., Kennedy, H., Chen, H., and Albers, J. J. Introduction of the human PLTP transgene suppresses the atherogenic diet-induced increase in plasma phospholipid transfer activity in C57BL/6 mice. Int. J. Clin. Lab Res. 29:14–21, 1999.

(16) Jiang, X. C., and Bruce, C. Regulation of murine plasma phospholipid transfer protein activity and mRNA levels by lipopolysaccharide and high cholesterol diet. J. Biol. Chem. 270:17133–17138, 1995.

(17) Beamer, L. J., Carroll, S. F., and Eisenberg, D. Crystal structure of human BPI and two bound phospholipids at 2.4 angstrom resolution. Science 276:1861–1864, 1997.

(18) Huuskonen, J., Wohlfahrt, G., Jauhiainen, M., Ehnholm, C., Teleman, O., and Olkkonen, V. M. Structure and phospholipid transfer activity of human PLTP: analysis by molecular modeling and site-directed mutagenesis. J. Lipid Res. 40: 1123–1130, 1999.

(19) Harlow, E., and Lane, D. Antibodies. A laboratory manual. Cold Spring Harbor: Cold Spring Harbor Laboratory, p.1–726.

Various publications in addition to the immediately foregoing are cited herein, the disclosures of which are incorporated by reference in their entireties. The citation of any reference herein should not be deemed as an admission that such reference is available as prior art to the instant invention.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A process of increasing reverse cholesterol transport in a mammal by administering camptothecin or a camptothecin derivative selected from the group consisting of topotecan, 9-NH2-CPT(S), and 9-NH2-10,11-MD-CPT(S), in an amount sufficient to promote the increased expression of phospholipids transfer protein (PLTP).

2. The process of claim 1 wherein said mammal has familial hypercholesterolemia (PH) with either hetero- or homo-zygotic deficiencies in the receptors for the low density lipoprotein (LDL) particles.

3. The process of claim 1 for use in lowering cholesterol levels in a mammal with a disease selected from the group consisting of Tangier's disease, familial HDL deficiency disease, and other diseases associated with deficiencies in uptake and removal of lipid molecules.

4. The process of claim 1 for use in treating FH patients who are either wholly LDL receptor negative (LDL receptor$^{-/-}$), or are partially deficient in LDL receptor (LDL receptor$^{+/-}$).

5. The process of claim 1 for treating patients with high cholesterol levels and who are refractory to conventional therapy for lowering cholesterol.

6. The process of claim 4 additionally comprising the simultaneous or sequential administration of other lipid lowering agents selected from the group consisting of the statins, niacin, bile acid-binding resin, and fibrate.

7. The process of claim 5 for treating patients with Tangier's disease and familial HDL deficiency disease, additionally comprising the simultaneous or sequential administration with other lipid lowering agents selected from the group consisting of the statins, niacin, bile acid-binding resin, and fibrate.

8. The process of claim 5 for treating people with high cholesterol levels and who are refractory to conventional therapy for lowering cholesterol, additionally comprising treatment with other lipid lowering agents selected from the group consisting of the statins, niacin, bile acid-binding resin, and fibrate.

9. A method of treating hyperlipidemia using camptothecin or a camptothecin derivative selected from the group consisting of topotecan, 9-NH2-CPT(S), and 9-NH2-10,11-MD-CPT(S) that induces phospholipids transfer protein levels to increase reverse cholesterol transport and to lower cholesterol.

10. A method of treating hyperlipoproteinemia using camptothecin or a camptothecin derivative selected from the group consisting of topotecan, 9-NH2-CPT(S), and 9-NH2-10,11-MD-CPT(S) that induces phospholipids transfer protein levels to increase reverse cholesterol transport and to lower cholesterol.

11. A method of claim 9 for treating hyperlipidemia, additionally comprising the simultaneous or sequential treatment with other lipid lowering agents selected from the group consisting of the statins, niacin, bile acid-binding resin, and fibrate.

12. A method of claim 10 for treating hyperlipoproteinemia, additionally comprising the simultaneous or sequential treatment with other lipid lowering agents selected from the group consisting of the statins, niacin, bile acid-binding resin, and fibrate.

13. A method of lowering cholesterol levels in a mammal with detectably high blood cholesterol levels by increasing phospholipids transfer protein gene expression comprising administering a pharmaceutical composition comprising camptothecin or a camptothecin derivative selected from the group consisting of topotecan, 9-NH2-CPT(S), and 9-NH2-10,11-MD-CPT(S).

14. A method of treating patients having diseases associated with high cholesterol levels comprising administering a pharmaceutical composition comprising camptothecin or the camptothecin derivatives of claim 13.

15. The method of claim 14 wherein said diseases are selected from the group consisting of Tangier's disease, familial HDL deficiency disease, and other diseases associated with deficiencies in uptake and removal of lipid molecules.

* * * * *